(12) United States Patent
Waheed et al.

(10) Patent No.: US 7,674,629 B2
(45) Date of Patent: Mar. 9, 2010

(54) METHOD FOR IMPROVING CHEMILUMINESCENT SIGNAL

(75) Inventors: Abdul Waheed, Valley Park, MO (US); Michael A. Moxley, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 12/049,131

(22) Filed: Mar. 14, 2008

(65) Prior Publication Data

US 2009/0233369 A1 Sep. 17, 2009

Related U.S. Application Data

(60) Provisional application No. 60/895,127, filed on Mar. 15, 2007.

(51) Int. Cl.
*G01N 21/76* (2006.01)
*G01N 31/00* (2006.01)

(52) U.S. Cl. .............................. 436/172; 436/8; 436/18; 436/135; 436/164; 436/166; 436/176; 252/408.1; 252/700

(58) Field of Classification Search ..................... 436/8, 436/18, 86, 100, 135, 164, 166, 172, 174, 436/176; 252/408.1, 700
See application file for complete search history.

(56) References Cited

U.S. PATENT DOCUMENTS

| 5,306,621 | A  | * | 4/1994  | Kricka ........................ 435/7.91 |
| 5,922,558 | A  | * | 7/1999  | Akhavan-Tafti ............... 435/28 |
| 6,602,679 | B2 | * | 8/2003  | Giri .............................. 435/28 |
| 2003/0073150 | A1 | * | 4/2003 | Woerner et al. ............. 435/7.92 |
| 2005/0272108 | A1 | * | 12/2005 | Kalra et al. ................. 435/7.92 |

OTHER PUBLICATIONS

Sanchez et al. Analytica Chimica Acta, vol. 310, 1995, pp. 399-406.*
Sanchez et al. Journal of Luminescence, vol. 65, 1995, pp. 33-39.*
Yakunin, Alexander F. and Hallenbeck, Patrick C. (1998) A Luminol/Iodophenol Chemiluminescent Detection System for Western Immunoblots. Analytical Biochemistry 258 (1), pp. 146-149, Copyright by Academic Press (1998).
Towbin, H.T., Staehelin, T., and Gordon, J. (1979) Electrophoretic Transfer Of Proteins From Polyacrylamide Gels to Nitrocellulose Sheets Procedure and Some Applications. Proceedings of the National Academy of Science USA, vol. 76, pp. 4350-4354.
Vachereau, A. (1989) Luminiscent Immunodetection of Western Blotted Proteins from Coomassie Stained Polyacrylamide Gel. Analytical Biochemistry 179, pp. 206-208, Copyright by Academic Press, Inc (1989).
Waheed, A., Zhu, X.L., and Sly, W.S. (1992) Membrane Associated Carbonic Anhydrase from Rat Lung. The Journal of Biological Chemistry, vol. 267, No. 5: pp. 3308-3311, Copyright by The American Society for Biochemistry and Molecular Biology, Inc., U.S.A. (1992).
Bonapace, G., Waheed, A., Shah, G.N., and Sly, W.S. (2004) Chemical Chaperones Protect from Effects of Apoptosis Inducing Mutation in Carbonic Anhydrase IV Identified in Retinitis Pigmentosa 17. Proceedings of the National Academy of Sciences USA, vol. 101, pp. 12300-12305, Copyright by The National Academy of Sciences of the USA (2004).
Bostick, D.T. and Hercules, D.M. (1975) Quantitative Determination of Blood Glucose Using Enzyme Induced Chemiluminescence of Luminol. Analytical Chemistry, vol. 47, No. 3, pp. 447-452.
Zhu, X.L. and Sly, W.S. (1990) Carbonic Anhydrase IV from Human Lung. Purification, Characterization, and Comparison with Membrane Carbonic Anhydrase from Human Kidney. The Journal of Biological Chemistry, vol. 265, No. 15, pp. 8795-8801, Copyright by The American Society for Biochemistry and Molecular Biology, Inc., U.S.A. (1990).
White, B.H., and L.K. Kaczmarek. (1997) Identification of a Vesicular Pool of Calcium Channels in the Bag Cell Neurons of Aplysia Californica. The Journal of Neuroscience, vol. 17, No. 5, pp. 1582-1595, Copyright by Society for Neuroscience (1997).
Gallagher S (1995) Visualization with Luminescent substrates. in: Current Protocols in Molecular Biology (Ausubel F, Brent R, Kingston RE, Moore DD, Seidman JG, Smith JA, Struhl K, eds), pp. 10.8.12-10.8.24. New York: Wiley.

(Continued)

*Primary Examiner*—Maureen M Wallenhorst
(74) *Attorney, Agent, or Firm*—Mark E. Stallion; Husch Blackwell Sanders LLP

(57) ABSTRACT

The present invention is directed to compositions and methods for improving a chemiluminescent signal. In particular, a reaction buffer with an alkaline pH range of about 9 to 10 provides a maximal chemiluminescent intensity and longevity of luminol that is catalyzed by superoxide anions. The addition of carbonate to the reaction buffer provides an optimal signal to background ratio and stability of a chemiluminescent signal from luminol catalyzed by superoxide anions. The method includes preparing a buffer with an alkaline pH, combining the buffer with a working reagent to produce and detect a chemiluminescent signal. The working reagent includes luminol, a coumaric acid and a peroxide. The composition includes a buffer having a pH from about 9 to about 10, a stock reagent comprising luminol, a coumaric acid, a peroxide, and a second buffer having a pH of about 8.5.

10 Claims, 5 Drawing Sheets

OTHER PUBLICATIONS

White, Benjamin H. and Kaczmarek, Leonard K. (1997) Identification of a Vesicular Pool of Calcium Channels in the Bag Cell Neurons of Aplysia californica. The Journal of Neuroscience, vol. 17, No. 5, pp. 1582-1595, Copyright by Society for Neuroscience (1997).

ECL reagent: homegrown version; http://celljunctions.med.nyu.edu/lab/notprivate/methods-html/ECL.html, date unknown.

Homemade ECL; The Chin-Sang Lab; http://130.15.90.245/homemade_ecl.htm; Queen's University, Kingston, ON, Canada, date unknown.

Home made ECL Cheap, Quick Reliable; http://www.geocities.com/CollegePark/Den/1291/protocols/lumin.html, date unknown.

* cited by examiner

Luminol

Aminophthatlate ion

Figure 2a
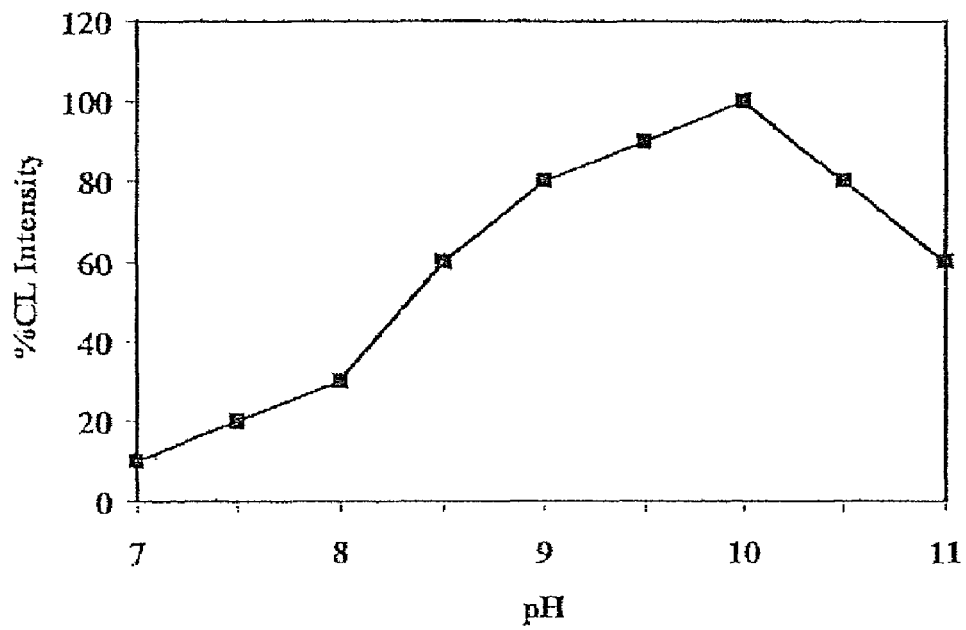
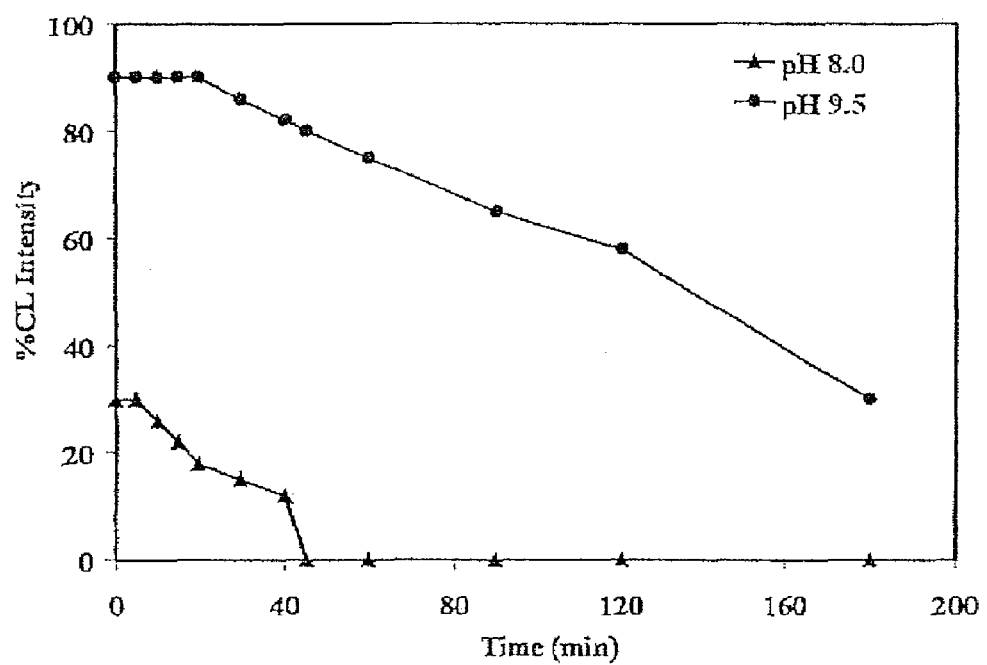
Figure 2b

METHOD FOR IMPROVING CHEMILUMINESCENT SIGNAL

CROSS-REFERENCE TO RELATED APPLICATIONS

This application is a non-provisional of and claims priority to U.S. Provisional Patent Application Ser. No. 60/895,127, filed Mar. 15, 2007, which document is hereby incorporated by reference herein to the extent permitted by law.

STATEMENT REGARDING FEDERALLY SPONSORED RESEARCH OR DEVELOPMENT

None.

BACKGROUND OF THE INVENTION

The present invention generally relates to compositions and methods of detecting molecular interactions, such as protein interaction, in the fields of research, medical diagnostics, and DNA research. Various methods have been developed to study steady state levels, biosynthesis and turnover, mutation and stability, and effects of pharmacological compounds on expression.

Western blots are commonly used to detect proteins. A SDS-PAGE (sodium dodecyl sulfate polyacrylamide gel electrophoresis) technique is first used to separate proteins according to their electrophoretic mobility (a function of length of polypeptide chain or molecular weight as well as higher order protein folding, post translational modification and other factors). Following the SDS-PAGE of protein samples and electrophoretic transfer of protein polypeptides from the polyacrylaminde gel to PVDF (polyvinylidene fluoride) or nitrocellulose membranes, polypeptides are identified using protein specific primary antibodies, secondary antibody conjugates of peroxidase or alkaline phosphatase enzymes, and chromogenic or chemiluminescent substrates of peroxidase or alkaline phosphatase enzymes. Protein detection is limited by chromogenic substrates and the read out of results on a western blot is inconvenient, difficult and often not accurate. These difficulties led to the use of chemiluminescent substrates for peroxidase or alkaline phosphatase or other enzymes. This is also a convenient method to detect protein polypeptides on western blotting by using X-ray film.

FIG. 1 illustrates the mechanism of a chemiluminescence reaction. In the chemiluminescence reaction luminol or isoluminol is catalyzed by superoxide anions in a solution with an alkaline pH. Luminol is converted to aminophthalate ions by superoxide anions produced from hydrogen peroxide or sodium perborate by a peroxidase enzyme at alkaline pH. Superoxide anions convert luminol or isoluminol to aminothalate ions which give rise to chemiluminescence light of 430 nm. This light can be recorded by a luminometer or detected on X-ray film. A strong and stable chemiluminescence signal of luminol depends on the alkaline pH of the reaction because strong and stable chemiluminescence is due to the presence of stable aminothalate ions providing enhanced luminescence. Therefore, it would be beneficial to provide a composition and a method for producing the same that has stable aminothalate ions thereby enhancing the chemiluminescence and the detection of proteins and other substances.

The following references that are cited throughout this disclosure are incorporated herein by reference in their entirety to the extent permitted by law. These references merely serve to support the invention and to provide background and context. Applicant reserves the right to challenge the veracity of any statement made therein.

Yakunin, Alexander F. and Hallenbeck, Patrick C. A Luminol/Iodophenol Chemiluminescent Detection System for Western Immunoblots. Analytical Biochemistry 258 (1), 146-149.

Towbin, H. T., Staehelin, T., and Gordon, J. (1979) Electrophoretic Transfer Of Proteins From Polyacrylamide Gels to Nitrocellulose Sheets Procedure and Some Applications. Proc. Natl. Acad. Sci. USA 76, 4350-4354.

Vachereau, A. (1989) Luminiscent Immunodetection of Western Blotted Proteins from Coomassie Stained Polyacrylamide Gel. Anal. Biochem. 179, 206-208.

Waheed, A., Zhu, X. L., and Sly, W. S. (1992) Membrane Associated Carbonic Anhydrase from Rat Lung. J. Biol. Chem. 267: 3308-3311.

Bonapace, G., Waheed, A., Shah, G. N., and Sly, W. S. (2004) Chemical Chaperones Protect from Effects of Apoptosis Inducing Mutation in Carbonic Anhydrase IV Identified in Retinitis Pigmentosa 17. Proc. Natl. Acad. Sci. USA 101, 12300-12305.

Bostick, D. T. and Hercules, D. M. (1975) Quantitative Determination of Blood Glucose Using Enzyme Induced Chemiluminescence of Luminol. Anal. Chem. 47, 447-452.

Zhu, X. L. and Sly, W. S. (1990) Carbonic Anhydrase IV from Human Lung. Purification, Characterization, and Comparison with Membrane Carbonic Anhydrase from Human Kidney. J. Biol. Chem. 265, 8795-8801.

White, B. H., and L. K. Kaczmarek. Identification of a Vesicular Pool of Calcium Channels in the Bag Cell Neurons of Aplysia Californica. J. Neurosci. 17, 1582-1595, 1997.

SUMMARY OF THE INVENTION

The present invention is directed to compositions and methods for improving a chemiluminescent signal. In particular, a reaction buffer with an alkaline pH range of about 9 to about 10 provides a maximal chemiluminescent intensity and longevity of luminol that is catalyzed by superoxide anions. The addition of carbonate to the reaction buffer provides an optimal signal to background ratio and stability of a chemiluminescent signal from luminol catalyzed by superoxide anions.

In one of many illustrative, non-limiting aspects of the present invention, there is provided herein a method for improving a chemiluminescent signal. The method includes preparing a buffer with an alkaline pH, combining the buffer with a working reagent to produce and detect a chemiluminescent signal. The working reagent includes luminol, coumaric acid and a peroxide.

In another of many illustrative, non-limiting aspects of the present invention, there is provided herein a chemical composition for improving a chemiluminescent signal. The composition includes a buffer having a pH from about 9 to about 10, a stock reagent comprising luminol, a coumaric acid, a peroxide, and a second buffer having a pH of about 8.5.

BRIEF DESCRIPTION OF THE SEVERAL VIEWS OF THE DRAWING

In the accompanying drawings that form a part of the specification and that are to be read in conjunction therewith:

FIG. 2A is a graphical representation illustrating the chemiluminescent intensity of luminol at different pHs with the maximum chemiluminescent intensity around pH 9.5.

FIG. 2B is a graphical representation of the chemiluminescent intensity of luminol at pH 8.0 and at pH 9.5 determined at different times.

DETAILED DESCRIPTION OF THE INVENTION

Figure 1:
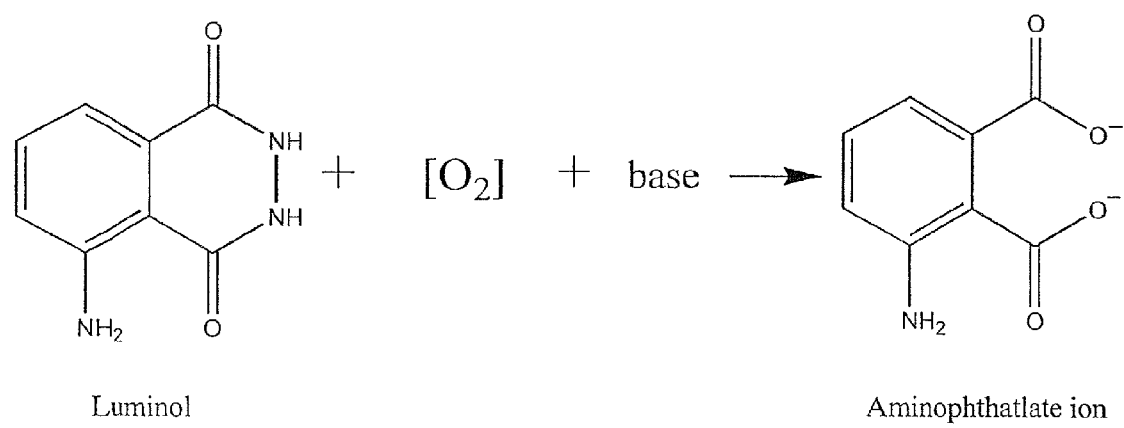
FIG. 1 is a representation of the mechanism of a chemiluminescence reaction of luminol catalyzed by superoxide anions at alkaline pH.

There is provided herein a method for improving a chemiluminescent signal. Improved chemiluminescent signal means improved results for the identification of molecular interactions, specifically protein interactions. Improved chemiluminescent signal is also applicable to DNA research. In one embodiment, a reaction buffer with an alkaline pH range of approximately 9 to provides a maximal chemiluminescent intensity and provides for the longevity of luminol catalyzed by superoxide anions. The addition of carbonate to the reaction buffer provides an optimal signal to background ratio and stability of a chemiluminescent signal from luminol catalyzed by superoxide anions.

In one embodiment, a method for enhancing a chemiluminescent signal includes the steps of buffering a buffer to a pH of preferably 7 to 10, more preferably of 9 to 10, and most preferably of 9.5, where the buffer includes a buffering agent, a perborate salt and a base, combining the buffer with a working reagent, wherein producing a chemiluminescent signal, and recording results. In one embodiment, the buffering agent is a carbonate, a phosphate, or a mixture thereof. In another embodiment, if the buffering component of the solution is sodium phosphate, it may be used between about 15 to about 150 mM. In another embodiment, if the buffering component of the solution is sodium carbonate, it may be used at about 50 mM. The base may be a sodium perborate salt, a potassium perborate salt, or a mixture thereof. In one embodiment, the perboarte is at about 10 mM. The working reagent may comprise luminol (3-aminophthalhydrazide) or isoluminol, a coumaric acid, and a peroxide. In one embodiment, luminal or isoluminol has a concentration from about 0.125 to about 1.25 mM. In one embodiment, the coumaric acid is p-coumaric acid and has a concentration from about 0.11 to about 3.52 mM. The peroxide may be hydrogen peroxide or sodium perborate. In one embodiment, hydrogen peroxide has a concentration from about 2.7 to about 15 mM. A preferred buffer comprises 50 mM $NaPO_4$, 50 mM $NaCO_3$, 150 mM NaCl, and 10 mM $NaBO_3.4H_2O$. The chemiluminescence signal or light that is produced by the reaction may be recorded by a luminometer, detected on X-ray film, and detected a digital imaging apparatus using a CCD camera. The signal produced is strong, stable, and long lasting chemiluminescent signal.

In another embodiment, the invention is directed to a chemiluminescence kit or composition including a first buffer having an alkaline pH, preferably between about 9 to about 10 and, most preferably 9.5, a stock reagent that is luminol, a coumaric acid stock, a peroxide, preferably hydrogen peroxide, sodium perborate, or a mixture thereof, and a second buffer having a pH of about 8.5, the second buffer preferably comprising about 100 mM trishydroxymethylaminomethane (Tris).

In an illustrative example, the chemiluminescent intensity of luminol catalyzed by superoxide anions produced from hydrogen peroxide or sodium perborate by secondary antibody conjugated peroxidase at different pHs ranging from pH 7 to 11. 20 ng of recombinant human carbonic anhydrase IV was spotted on a PVDF-membrane. The membrane was blocked with 2% casein in a TBST buffer. The TBST buffer was made with 10 mM Tris HCl pH 7.5, 150 mM NaCl, and 0.01% Tween-20. The membranes were incubated with 1:5000 dil rabbit anti-human carbonic anhydrase anti-serum at 24° C. for 2 hours, then the membranes were washed 5×5 minutes each with the TBST buffer and incubated with secondary antibodies conjugated with peroxidase at 1:3000 dil at 24° C. for 1.5 hours. The membranes were washed with the TBST buffer, 5×5 minutes each and incubated with 25 µg/ml luminol or isoluminol, 25 µg/ml 4-iodophenol enhancer, and 0.01% $H_2O_2$ as peroxidase substrate in a luminol buffer. The luminol buffer was made with 50 mM $NaPO_4$, 50 mM NaCO3, and 150 mM NaCl. The membranes were incubated at different pHs ranging from about pH 7 to about pH 11 at 24° C. for 1 minute before chemiluminescent (CL) intensity was recorded on X-ray film. The CL intensity of the spots were quantitated by photo imaging software. The percent CL intensity at the different pHs, was calculated from the maximum CL intensity assuming 100% at a pH range of 9.5-10.5. The results in FIG. 2A illustrate that the highest CL intensity was between pH 9.5 and 10.5. Below pH 9 and above pH 10 CL intensities were decreased. The optimum pH for maximum CL intensity was found to be pH 9.5-10. From these results, it is concluded that pH below 9.0 (e.g. pH 8-8.5) is not an optimum condition for CL intensity which is generally recommended in commercially enhanced chemiluminescent reagents (ECL).

In another illustrate example, the CL intensity and stability was tested and compared at pH 8.0 and 9.5. The results are illustrated in FIG. 2B and showed that the relative CL intensity at pH 8.0 was lower and decreased with a half life of 20 minutes. However, the relative CL intensity at pH 9.5 was high and decreased very slowly. Even after 3 hours, 30% of the CL intensity remained and was comparable to the intensity of the CL initially observed at pH 8.0. From this information it is concluded that CL intensity of luminol is highest near pH 9.5 and CL intensity is very long lasting. This has several technical advantages over lower alkaline pH, e.g. pH 8-8.5.

Figure 3:
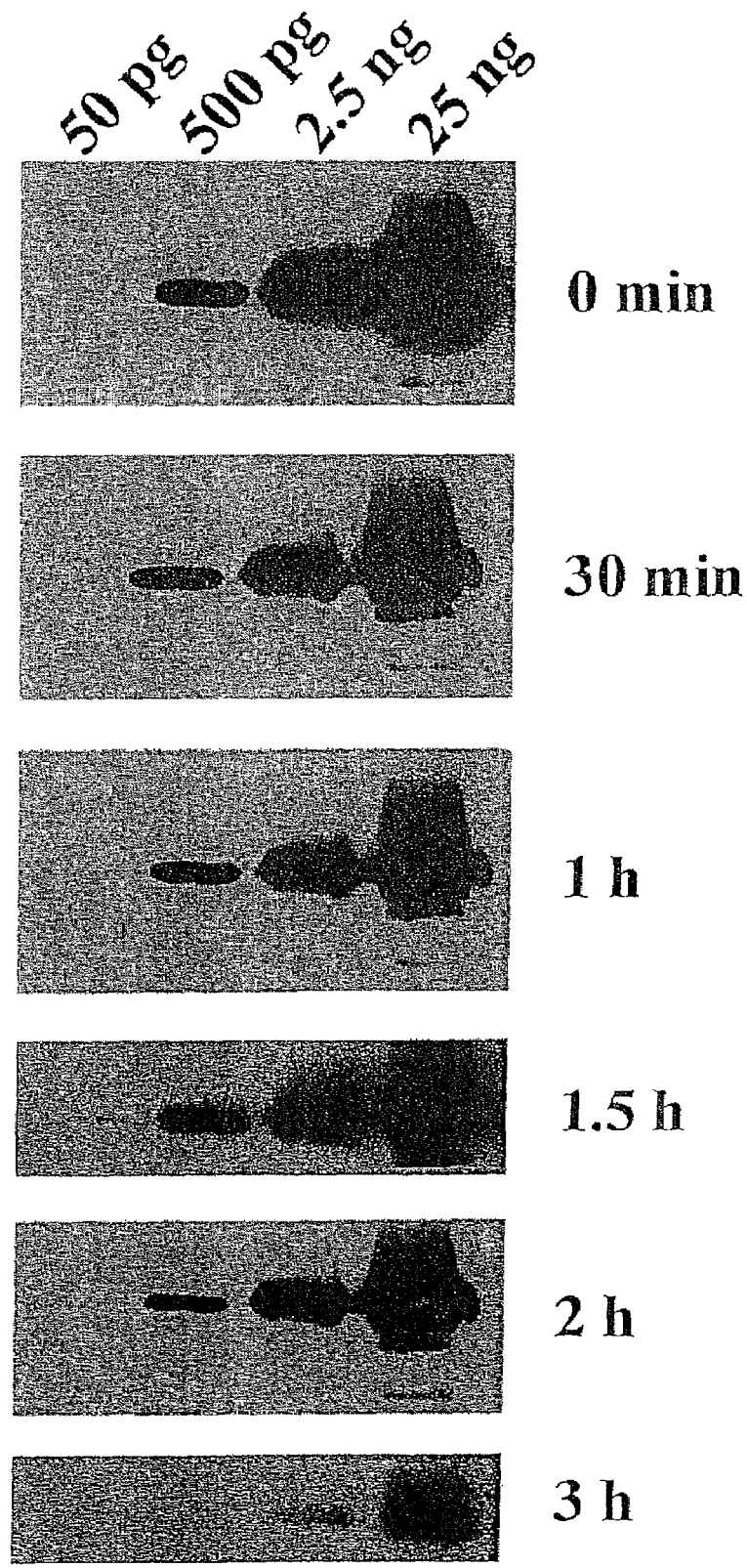
FIG. 3 is a Western blot analysis of carbonic anhydrase IV.

In another illustrative example, the results of which are summarized in FIG. 3, the sensitivity and stability of the luminol reaction was determined for about pH 9.5 in western blot analysis. Recombinant human carbonic anhydrase IV enzyme from 50 pg to 25 ng proteins was analyzed by SDS-PAGE. After the electrophoretic separation the polypeptides were electrophoretically transferred to PVDF membranes using a known Transblot technique. For immunodetection the membranes were incubated, first with a blocking buffer (2% casein in a TBST buffer made similarly as described herein) at 24° C. for 15 to 30 minutes and incubated with rabbit anti-human CA4 antiserum 1:5000 dil in the TBST buffer at 4° C. overnight. After washing the membrane with the TBST buffer for 5×5 minutes each, the membranes were incubated with secondary antibodies conjugated with peroxidase at 1:5000 dil in TBST at 24° C. for 1.5 hours. The membranes were washed with the TBST buffer for 5×5 minutes each and incubated with 25 µg/ml luminol or isoluninol, 25 µg/ml 4-iodophenl, 0.01% $H_2O_2$ in a pH 9.5 luminol buffer for 5 minutes. The membranes were stored for zero to 3 hours before being exposed to X-ray film. For zero time storage one membrane was exposed immediately to X-ray film for 1 minute. Other membranes were stored in the dark for 30 to 180 minutes at 24° C. before being exposed to X-ray film for 1 minute. At zero time, at all concentrations of carbonic anhydrase IV from 50 pg to 25 ng, the polypeptides for carbonic anhydrase IV were detected. After 30 to 90 minutes of storage, the apparent CL intensity of the polypeptide was reduced; however, the polypeptides at 50 pg were still visible. After 2 hours the CL intensity of 50 pg peptide was hard to see, but the polypeptide intensity at 500 pg was still very strong. However, after 3 hours of storage, 2.5 ng and 25 ng protein polypeptides were still visible with reduced intensity. Similar results have been reported using different buffer systems (as illustrated in the Yakunin and Hallenbeck references); however, the detection limit was not as sensitive as the present invention.

Figure 4:
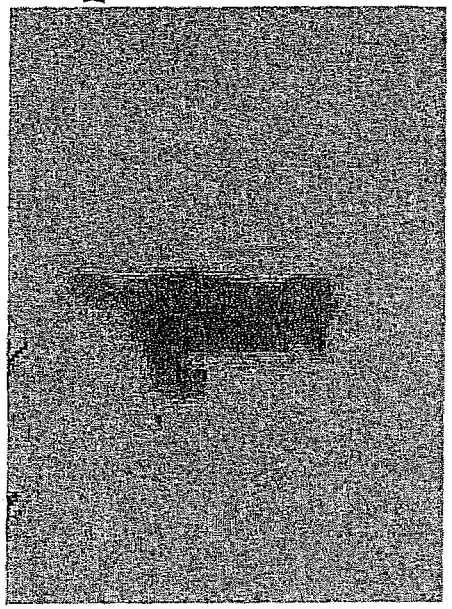
FIG. 4 is a Western blot analysis of raw 264.7 cells ($4 \times 10^5$/400 µl) that were incubated for 24 hours in the presence of 10 µg/ml of LPS.
Figure 4:
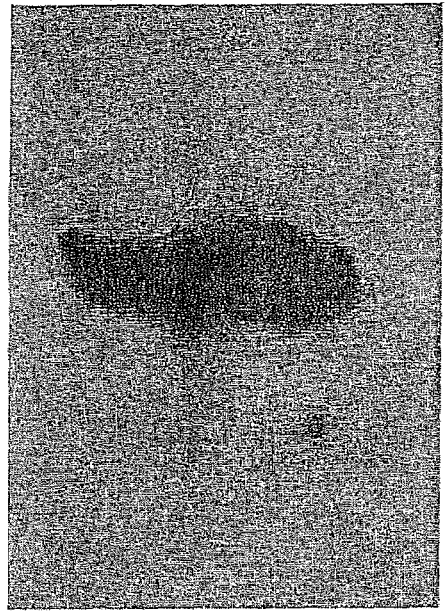

In another illustrative example, the results of which are illustrated by FIG. 4, the effect of pH on CL intensity using another primary antibody and nitrocellulose membrane was evaluated. RAW 264.7 cells ($4 \times 10^5/400$ μl) were incubated for 24 hours in the presence of 10 μg/ml of LPS. Equal amounts of a SDS lysate of the cells were subjected to polyacrylamide gel electrophoresis and transferred to a nitrocellulose membrane. The membrane was blocked by incubation for 1 hour in 5% nonfat milk in a TBST buffer. The blot was then incubated overnight with rabbit anti iNOS (1:1000) in the TBST buffer. The blot was washed three times and incubated with donkey anti rabbit IgG-HRP conjugate (1:5000). The membrane was washed and divided. Half of the blot was exposed to a homemade chemiluminescent reagent modified from White and Kaczmarek with a pH of 8.5 and including 1.25 mM luminol, 0.2 mM coumaric acid and 0.01% $H_2O_2$. The other half of the blot was incubated with the same reagent adjusted to a pH of 9.5. The signal obtained at higher pH is stronger than that observed at the lower pH (pH 8.5).

Figure 5:
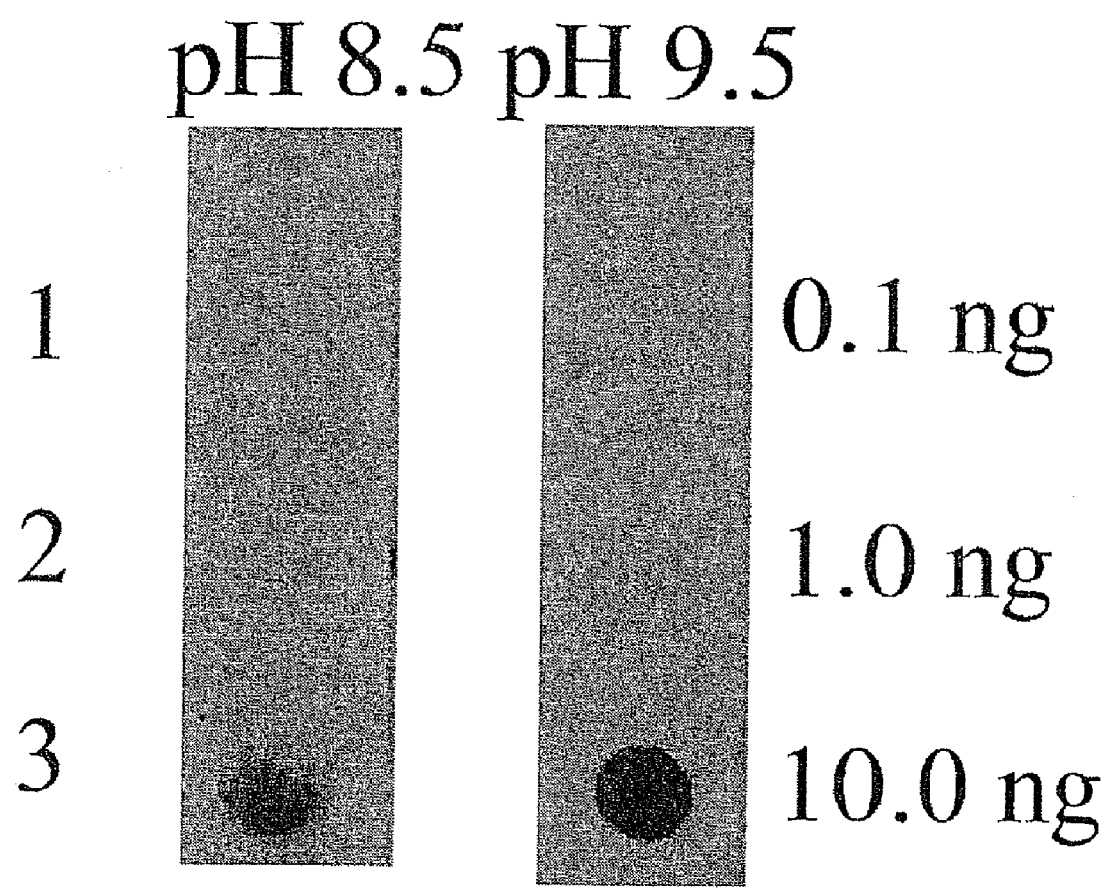
FIG. 5 is a Western blot analysis where increasing amounts of biotinylated DNA were applied to a nitrocellulose membrane in duplicate.

In another illustrative example, the results of which are illustrated in FIG. 5, the optimized reagent was also used to compare the luminol signal obtained from nucleic acid dot blots at pH 8.5 and pH 9.5. Increasing amounts of biotinylated DNA were applied to a nitrocellulose membrane in duplicate. The membrane was blocked by incubating it with 5% nonfat milk in a TBST buffer. The dot blot was then incubated with 0.1 μg/ml streptavidin HRP conjugate for 30 minutes. The membrane was washed and divided. Half the membrane was stained with the described ECL reagent at pH 8.5 and the other half at pH 9.5. The signal obtained at the higher pH is considerably stronger as seen in FIG. 5. From these results we concluded that the present luminol buffer with alkaline pH is very valuable in detecting a low amount of proteins or nucleic acid for a prolonged time in western blots or dot blots.

The method and composition provided herein improves chemiluminescent signal and increases the signals strength and longevity providing improved results for the identification of molecular interactions, specifically protein interactions.

From the foregoing it will be seen that this invention is one well adapted to attain all ends and objects hereinabove set forth together with the other advantages which are obvious and which are inherent to the structure.

The various embodiments of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention. The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A method for improving a chemiluminescent signal comprising the steps of:
    preparing a buffer with an alkaline pH wherein said buffer comprises a buffering agent, a perborate salt, and a second salt;
    combining said buffer with a working reagent wherein said reagent includes luminol, coumaric acid and a peroxide;
    producing a chemiluminescent signal; and
    detecting said chemiluminescent signal.

2. The method of claim 1 wherein said buffer has a pH from about 9 to about 10.

3. The method of claim 1 wherein said alkaline pH is about 9.5.

4. The method of claim 1 wherein said peroxide is selected from the group consisting of hydrogen peroxide, sodium perborate, and mixtures thereof.

5. The method of claim 1 wherein said chemiluminescent signal is detected by a device wherein said device is selected from the group consisting of a luminometer and a X-ray film.

6. A chemical composition for improving a chemiluminescent signal comprising:
    a first buffer having an alkaline pH;
    a stock reagent wherein said reagent is luminol;
    a coumaric acid stock;
    a peroxide; and
    a second buffer;
    wherein said first buffer comprises 50 mM $NaPO_4$, 50 mM $NaCO_3$, 150 mM NaCl, and 10 mM $NaBO_3 \cdot 4H_2O$.

7. The composition of claim 6 wherein said first buffer has a pH from about 9 to 10.

8. The composition of claim 6 wherein said first buffer has a pH of about 9.5.

9. The composition of claim 6 wherein said peroxide is selected from the group consisting of hydrogen peroxide, sodium perborate, and mixtures thereof.

10. The composition of claim 6 wherein said second buffer has a pH of about 8.5 and comprises about 100 mM trishydroxymethylaminomethane.

* * * * *